US011376392B2

(12) United States Patent
Kirchberger et al.

(10) Patent No.: US 11,376,392 B2
(45) Date of Patent: Jul. 5, 2022

(54) TUB FOR USE IN A HUMIDIFIER

(71) Applicant: ResMed Pty Ltd, Bella Vista (AU)

(72) Inventors: Andreas Kirchberger, Miesbach (DE);
Johannes Nickol, Neukenroth (DE);
Jens Rothfuss, Unterschleissheim (DE);
Johann Sebastian Burz, Germaringen
(DE); Robert Eibl, Bad Toelz (DE);
Christian Bayer, Penzberg (DE);
Bernd Christoph Lang, Graefelfing
(DE); Andreas Eibl, Munich (DE);
Martin Kasparbauer, Munich (DE)

(73) Assignee: ResMed Pty Ltd, Bella Vista (AU)

( * ) Notice: Subject to any disclaimer, the term of this patent is extended or adjusted under 35 U.S.C. 154(b) by 662 days.

(21) Appl. No.: 15/961,017

(22) Filed: Apr. 24, 2018

(65) Prior Publication Data
US 2019/0321580 A1  Oct. 24, 2019

(51) Int. Cl.
A61M 16/16  (2006.01)
A61M 16/10  (2006.01)
(Continued)

(52) U.S. Cl.
CPC ...... A61M 16/162 (2013.01); A61M 16/0066 (2013.01); A61M 16/109 (2014.02);
(Continued)

(58) Field of Classification Search
CPC .............. A61M 16/162; A61M 16/109; A61M 16/0066; A61M 2205/3331; A61M 2205/3334; A61M 2205/3368; A61M 2205/3379; A61M 2207/00; A61M 16/161; A61M 2205/3389; A61M 2205/3653; A61M 2205/0216; A61M 2205/0238; A61M 2207/10; A61M 16/16; A61M 16/0003; A61M 16/1075;
(Continued)

(56) References Cited

U.S. PATENT DOCUMENTS 4,028,444 A  6/1977 Brown et al.
4,782,832 A  11/1988 Trimble et al.
(Continued)

FOREIGN PATENT DOCUMENTS

AU  2008202098 A1  2/2009
AU  2014221312 A1  3/2015
(Continued)

OTHER PUBLICATIONS

WIPO Machine Translation, EP2848277A1, Accessed Sep. 11, 2020 (Year: 2020).*
(Continued)

Primary Examiner — Elliot S Ruddie
(74) Attorney, Agent, or Firm — Nixon & Vanderhye P.C.

(57) ABSTRACT

The present invention relates to a tub configured to receive a volume of liquid for a humidifier, comprising at least one plastic component and at least one metal component, which together form a space for receiving said volume of liquid, wherein the at least one metal component and the at least one plastic component are attached to each other by means of a silicone seal. Furthermore, the invention relates to method for manufacturing a tub for a humidifier.

34 Claims, 8 Drawing Sheets

(51) Int. Cl.
  *A61M 16/00*   (2006.01)
  *B29C 45/14*   (2006.01)
  *B29C 45/16*   (2006.01)
  *B29K 69/00*   (2006.01)
  *B29K 83/00*   (2006.01)
  *B29K 705/12*  (2006.01)
  *B29L 31/00*   (2006.01)

(52) U.S. Cl.
  CPC ............... *A61M 2205/3331* (2013.01); *A61M 2205/3334* (2013.01); *A61M 2205/3368* (2013.01); *A61M 2205/3379* (2013.01); *A61M 2207/00* (2013.01); *B29C 45/14336* (2013.01); *B29C 45/14778* (2013.01); *B29C 45/1671* (2013.01); *B29K 2069/00* (2013.01); *B29K 2083/00* (2013.01); *B29K 2705/12* (2013.01); *B29L 2031/762* (2013.01)

(58) Field of Classification Search
  CPC ...... A61M 2016/0027; A61M 2205/50; B29C 45/14336; B29C 45/14778; B29C 45/1671; B29K 2069/00; B29K 2083/00; B29K 2705/12; B29L 2031/762; F24F 6/00; F24F 2006/008
  See application file for complete search history.

(56) References Cited

U.S. PATENT DOCUMENTS

| | | | |
|---|---|---|---|
| 4,944,310 | A | 7/1990 | Sullivan |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 2004/0050386 | A1 | 3/2004 | Levine |
| 2006/0055069 | A1 | 3/2006 | DiMatteo et al. |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2014/0083431 | A1* | 3/2014 | Burz ................... A61M 16/06 128/206.24 |
| 2015/0030317 | A1* | 1/2015 | Bayer .................. F22B 1/284 392/403 |
| 2019/0055420 | A1* | 2/2019 | Beyer ................... C08K 3/34 |
| 2019/0134343 | A1* | 5/2019 | Letton ............... A61M 16/109 |
| 2019/0298964 | A1* | 10/2019 | Bayer ............... A61M 16/109 |

FOREIGN PATENT DOCUMENTS

| | | | | |
|---|---|---|---|---|
| AU | 2016904769 A1 * | 12/2016 | ............ | A61M 16/16 |
| DE | 20 2004 004 115 U1 | 7/2004 | | |
| EP | 2848277 A1 * | 3/2015 | .......... | A61M 16/109 |
| EP | 3 441 103 A1 | 2/2019 | | |
| WO | WO 98/004310 A1 | 2/1998 | | |
| WO | WO 98/034665 A1 | 8/1998 | | |
| WO | WO 00/21602 A1 | 4/2000 | | |
| WO | WO 2000/078381 A1 | 12/2000 | | |
| WO | WO 2004/073778 A1 | 9/2004 | | |
| WO | WO 2005/063328 A1 | 7/2005 | | |
| WO | WO 2006/074513 A1 | 7/2006 | | |
| WO | WO 2006/130903 A1 | 12/2006 | | |
| WO | WO 2007/019626 A1 | 2/2007 | | |
| WO | WO 2007/038152 A2 | 4/2007 | | |
| WO | WO 2009/052560 A1 | 4/2009 | | |
| WO | WO 2010/135785 A1 | 12/2010 | | |
| WO | WO 2010/140903 A1 | 12/2010 | | |
| WO | WO 2012/171072 A1 | 12/2012 | | |
| WO | WO 2013/020167 A1 | 2/2013 | | |
| WO | WO 2013/135318 A1 | 9/2013 | | |
| WO | WO 2014/138804 A1 | 9/2014 | | |
| WO | WO 2015/165845 A1 | 11/2015 | | |

OTHER PUBLICATIONS

Merriam-Webster, Definition of "overlap", accessed Mar. 10, 2021, https://www.merriam-webster.com/dictionary/overlap (Year: 2021).*
Extended European Search Report dated Sep. 3, 2019 in European Application No. 19170923.7, 11 pages.
"Respiratory Physiology", by John B. West, Lippincott Williams & Wilkins, 9$^{th}$ edition published 2012 (8 pages).
Communication Pursuant to Article 94(3) EPC dated Apr. 30, 2021 in European Application No. 19 170 923.7, 6 pages.

* cited by examiner

TUB FOR USE IN A HUMIDIFIER

1 BACKGROUND OF THE TECHNOLOGY

1.1 Field of the Technology

The present technology relates to one or more of the treatment, prevention and amelioration of respiratory-related disorders. The present technology also relates to medical devices or apparatus, and their use.

1.2 Description of the Related Art

1.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

1.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.2 Respiratory Pressure Therapy (RPT) Device

A respiratory pressure therapy (RPT) device may be used individually or as part of a system to implement one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

1.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

Respiratory humidifiers are available in many forms and may be a standalone device that is coupled to an RPT device via an air circuit, is integrated with the RPT device or configured to be directly coupled to the relevant RPT device. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or RPT device, and a gas outlet adapted to be connected to an air circuit that delivers the humidified gas to the patient interface.

Heated passover humidification is one common form of humidification used with an RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 CPAP devices respectively.

Other humidifiers may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

While a number of medical humidifiers are known, they can suffer from one or more shortcomings. Some medical humidifiers may provide inadequate humidification, some are difficult or inconvenient to use by patients. Furthermore, some humidifiers may be expensive to manufacture, therefore not every patient possibly benefitting from a humidifier may therefore be supplied with one. In addition, a humidifier and its liquid reservoir are required to be essentially fluid tight, especially during prolonged use and over a high number of heating cycles.

Therefore, a task of the present invention may be to provide a cost effective and fluid tight tub configured to receive a volume of liquid for use in humidifier. A second task of the present invention may be to provide a cost effective apparatus for humidifying a flow of air for delivery to a patient with little or no unintended fluid leakage. A third task of the present invention may be to provide a cost effective apparatus for treating a respiratory disorder in a patient. A fourth task of the present invention may be to provide a cost-effective and fast method for manufacturing of a humidifier tub configured to receive a volume of liquid.

2 BRIEF SUMMARY OF THE TECHNOLOGY

The present technology is directed towards providing medical devices used in the monitoring, amelioration, treatment, or prevention of respiratory disorders having one or more of improved comfort, cost, efficacy, ease of use and manufacturability.

A first aspect of the invention relates to a tub configured to receive a volume of liquid for use in a humidifier. The tub can also be called a reservoir, in particular a water reservoir. The volume configured to receive the liquid can also be called a reception space, reception volume, or simply volume or space.

The tub comprises at least one plastic component and at least one metal component, which together form the space for receiving said volume of liquid. In particular, the metal component can be configured to facilitate a heat transfer from a heat source, in particular an external heat source, in order to heat the liquid in the water reservoir. By heating the liquid, part of it can be vaporized and thus humidify an airflow. Preferably, the metal component forms at least a part of a bottom wall of the tub. The plastic component can reduce weight and/or production costs for the tub in comparison to a tub whose reception space is formed only by a metal component. The metal component can increase durability and efficiency of a humidifier with such a tub in comparison to a humidifier with tub whose reception space is formed only by a plastic component. The tub is particular suited for Passover humidification.

However, the attachment of the two components constitutes an additional manufacturing step that may increase overall costs. In addition, the connection between the metal component and the plastic component should be fluid tight to prevent unintended leakages.

Accordingly, the at least one metal component and the at least one plastic component are attached to each other by means of a silicone layer, which can preferably be a silicone seal. Such an attachment can be especially cost effective. In particular, if the silicone layer is configured as a silicone seal, unintended leakages can be prevented without requiring a seal in addition to an attachment means of the two components. Accordingly the number of parts can be reduced.

For example, the silicone layer can also be an interrupted silicone layer, in particular, comprising stripes, dots or other shapes. Any portion of the silicone part of the tub not actually having a sealing effect but nevertheless connected to the part of the silicone functioning as a seal can be considered as part of the silicone seal in the context of this application. For example, a complete inner silicone layer of the tub can still be designated as the silicone seal.

Preferably, the silicone seal is at least partially arranged between two adjacent surfaces of the plastic component and the metal component, in particular between any adjacent surfaces of the two components. Preferably, the silicone seal is arranged between any two respective surfaces of the metal component and the plastic component which face each other. In particular, there can only a small gap between those surfaces that is at least partially or completely filled by the silicone seal. The silicone seal can be arranged between any surfaces overlapping each other. Preferably, the silicone seal can be arranged between any two surfaces of the plastic component and the metal component that overlap each other in a top view, bottom view and/or in a view from the inside of the reception space.

The plastic component can comprise or consist of a polycarbonate. In particular, the plastic component can comprise or consist of a medical grade plastic material. The metal part can, for example, comprise or consist of a corrosion resistive metal, in particular stainless steel. The metal material of the metal component can be of a medical grade. Preferably, the silicone is made from a medical grade silicone, is odorless, is transparent, is non-toxic and/or is biocompatible.

In preferred embodiments of the tub, the silicone seal provides a fluid tight connection between the plastic component and the metal component. Therefore unintended leakages can be prevented. The silicone seal can then also be called a silicone fluid seal. In particular, the silicone seal is configured to continue to properly seal the attachment between the metal component and the plastic component during heating cycles of a humidifier. For example, the silicone seal can be adapted to absorb different thermal expansions of the metal component and the plastic component during use of the humidifier without allowing an unintended leakage or at least while still substantially maintaining its sealing function.

Another preferred embodiment of the tub, the silicone seal has a thickness between 0.01 mm and 0.2 mm, preferably less than 0.01 mm or 0.05 mm. Such a thickness of the silicone seal can provide a substantially rigid connection between the metal component and the plastic component despite using a silicone that is inherently flexible. In addition, a thin silicone seal can reduce manufacturing costs. The thickness of the silicone seal can, for example, be measured as a thickness of a layer of silicone and/or along an imaginary line perpendicular to and/or connecting the at least two surfaces of the plastic component and the metal component adjacent to each other, which can be sealed and/or connected by the silicone seal. The thickness of the silicone seal can also be defined as its smallest or average thickness. The thickness can also directly relate to a gap size between adjacent surfaces of the metal component and the plastic component.

In another preferred embodiment of the tub, at least a section of the metal component in contact with the silicone seal is treated with a silicone adhesion promoting agent and/or at least a section of the plastic component in contact with the silicone seal is a treated with a silicone adhesion promoting agent. Usually, silicone, especially when injection molded, only attaches to either plastic materials or metal materials. Therefore, to form a connection between the metal component and the plastic component, at least one of those components can be treated with an adhesion promoting agent. This allows permanent and secure connection of the silicone seal to both the metal component and the plastic component, in particular with one manufacturing step and/or during injection molding. For example, the adhesion promoting agent can be sprayed on, be a surface treatment, be a dotting of a material, be a plasma treatment and/or be a corona treatment.

Another preferred embodiment of the tub, the silicone seal is formed from liquid silicone rubber. Liquid silicone rubber can be easy to process and handle and may also provide a particular robust connection between the metal component and the plastic component.

In another preferred embodiment of the tub, the plastic component and/or the metal component are essential rigid. In particular, the plastic component and/or the metal component can be considered as non-flexible. By comparison, the silicone seal can be flexible and/or non-rigid. For example, the silicone seal can be more flexible, more elastic, and/or less rigid then the metal component and/or the plastic component. The plastic component and/or the metal component can be essentially non-compressible and/or non-stretchable. By comparison, the silicone seal can be stretchable and/or compressible. For example, the silicone seal can be more stretchable and/or compressible then the metal component and/or the plastic component.

In a further preferred embodiment of the tub, the plastic component is essentially trough shaped, having a bottom wall and surrounding sidewalls, extending from said bottom wall, wherein the bottom wall was a through hole, said through hole being closed, at least partially, by the metal component and said silicone seal. The side walls can also relate to one single continuous side wall forming a circumference of the tub. In a sectional view, such a side wall is then depicted as a plurality of side walls.

For example, the through hole is closed in a fluid tight manner by the metal component and the silicone seal. Not all components closing the through hole are required to be located outside of the through hole, below and/or above. For example, some or all components closing the through hole can be located inside the through hole. The metal component itself can substantially close the through hole while the silicone seal only closes the connection between the metal component and the plastic component, in particular a gap in-between. For example, the silicone seal can fill any remaining non-fluid tight gaps between the metal component and the plastic component.

In another preferred embodiment of the tub, the tub is essentially trough shaped, having a bottom wall and surrounding side walls, wherein the plastic component is essentially sleeve shaped and forms the side walls, while the bottom wall is essentially formed by the metal component. The silicone seal can also form a part of the side wall and/or bottom wall, in particular a minor part at the end of one or both components. Again, the side walls can relate to only one continuous side wall forming a circumference of the sleeve. The plastic component can also be ring and/or annular shaped. The plastic component can also be considered as a through with no bottom wall.

By comparison to a tub with the plastic component being trough shaped, as was described in the previous embodiment, a tub where the plastic component only forms the side walls can be easier and/or cheaper to manufacture. On the other hand, the previously described embodiment of a tub with a trough shaped plastic component can have a higher ratio of plastic component relative to other components, possibly resulting in a lighter and/or cheaper tub.

In another preferred embodiment of the tub, the metal component is attached to an inner side or an outer side of said side wall and/or to an inner side or an outer side of said bottom wall. The inner side of a wall can be defined as a side forming the liquid reception space. In particular, an inner side can be any side that can possibly come into contact with a liquid if the tub is filled. An inner side can be defined as the side of a wall facing the reception space. On the other hand, the outer side can be any side facing away from the space containing the liquid. Outer sides can be defined as sides opposite to inner sides. In particular, the outer side of any wall can usually not come into contact with a liquid filled into the tub. For a bottom wall, its inner side can be its upper side and its outer side can be its lower side. In this case, the upwards direction can be defined by the reception space of the liquid.

In another preferred embodiment of the tub, the metal component is shaped as and/or from a metal plate, preferably a substantially flat metal plate. In particular, the metal component can be a planer metal plate. Such a metal component is easy and cost effective to manufacture. In particular, such a metal component can be simply punched out from a metal sheet.

Another preferred embodiment of the tub, at least a portion of the metal component is dome-shaped, preferably in an outward direction. An outward direction can be defined similar to the inner and outer side. In particular, an outward direction can be a direction from an inner side to an outer side of a wall, a downward direction and/or can be a direction away from a center of the reception space. A dome-shape of the metal component can improve the connection to a heating apparatus, in particular to a heating apparatus with a flat heating plate. The dome-shape can improve heat transfer from a heating apparatus to the tub and thus to the liquid contained therein. The dome-shape of the metal component can result in the metal component curving outwardly convex when seen in a sectional view. The bottom wall of the tub can at least be partially dome-shaped away from the reception space for the liquid. Furthermore, the dome-shape may also allow further compensating thermal expansion of the metal component during use of the humidifier while also ensuring improved heat transfer. Preferably, the metal component is shaped as a dome-shaped metal plate.

In a further preferred embodiment of the tub, the metal component and the plastic component are only attached to each other by means of the silicone seal. Therefore, the silicone seal preferably not only functions as the fluids seal between the plastic and metal components but also is the only attachment means between those two components. Accordingly, there is no need for additional connection means that may increase costs, number of parts, weight and/or manufacturing steps. Connection between the metal component and the plastic component only by the silicone seal may also offer advantages for the thermal expansion compensation between the two components.

Alternatively or additionally, the metal component and the plastic component can also be fixed to each other by additional connection means, such as screws, clamps, a snap on connection or some form of permanent bonding such as welding or gluing. In this case, the silicone seal, while also enforcing the connection, primarily functions as seal that closes any non-fluid tight gap remaining between the two components. [61] Another preferred embodiment of the tub, at least a portion of the metal component and at least a portion of the plastic component overlap each other, and the silicone seal is at least arranged between the overlapping portions of the metal component and the plastic component. In particular, the silicone seal can be arranged in any overlapping portions, wherein overlapping portions are defined as those overlaps seen from the space for receiving said volume of liquid. Alternatively or additionally, the silicone seal can be arranged in any overlapping portion seen in a top view, seen from above, in a bottom view and/or seen from below of the tub. In particular, the silicone can be exclusively arranged in between the overlapping portions. This may reduce the amount of silicone required for the tub.

Another preferred embodiment of the tub, the silicone seal covers at least a portion of the metal component, the portion of the metal component not overlapping with the plastic component; and/or the silicone seal covers at least a portion of the plastic component, the portion of the plastic component not overlapping with the metal component. Accordingly, the silicone seal can extend beyond any overlapping portion. This may further improve thermal expansion compensation of the two components. Furthermore, the seal and connection can be more robust, especially during thermal expansion and contraction of the components. The silicone seal can thus also protect parts of the surfaces of the metal component and the plastic component. For example, the silicone seal can also comprise a silicone layer covering parts or all of the inner surfaces of the tub. This silicone layer can be an interrupted silicone layer, possibly having stripes, dots or other shapes.

Another preferred embodiment of the tub, the silicone layer, in particular the silicone seal further covers at least a portion of the metal part or the plastic part for surface protection, in particular parts or all of any surface forming the reception space of the tub. In this case, the silicone layer respectively the silicone seal can also be considered or act as a protective coating. In particular, if the whole surface of the metal component that could otherwise come in contact with the liquid contained in the reception space is covered with the silicone seal, a non-corrosive resistant metal or at least a less corrosive resistant metal can be used for the metal component. The inner surface coating of the metal component with the silicone seal may prevent corrosion. Accordingly, material costs may be reduced. The silicone seal can also cover at least a part of the plastic component, particularly a section forming part of the bottom wall and/or at least a section forming a part of the side wall.

The silicone seal can cover at least a portion of the metal component and/or the plastic component in a region where there is no overlap between the metal component and the plastic component. For example, the silicone seal can cover a surface of one of the components that would be otherwise accessible in the absence of the component. In particular, the silicone seal can act as a protective coating on a surface side of the metal component facing the reception space and/or of a surface side of the plastic component and facing the reception space. The silicone seal can also be a silicone cover of the metal component. The silicone cover can be any part of the silicone seal not acting as an attachment between the metal components in the plastic component. In particular, a part of the silicone seal can be configured as a silicone cover layer covering at least a part of the metal component otherwise in direct contact with the space for receiving said volume of liquid. Preferably, the silicone seal covers any portion of the metal component and/or the plastic component forming the surface of the reception space for the liquid.

Another preferred embodiment of the tub, an entire inner surface of the metal component facing the space for receiving said volume of liquid is coated with the silicone seal, in particular in the form of a silicone layer on the surface of the metal component facing the space for receiving said volume of liquid. Preferably, the layer covering said surface is a thin layer so as not to inhibit heat transfer from a heat source to the liquid containing the reception space. Preferably, more than 70%, 80%, 90% or an entire side of the metal component at least partially facing the holding space is covered by the silicone seal. In particular, this is preferable in a case where the metal component is shaped as a metal plate or dome-shaped metal plate.

Another preferred embodiment of the tub, the silicone seal is formed as a labyrinth seal and/or as a seal providing a spring effect, in particular by comprising a silicone spring element. For example, a silicone spring element may be a meandered section of the silicone seal and/or a silicone layer. Another example of a silicone spring element is a silicone part that is curving back on itself. Another example of a silicone spring element may be a section curved in respect to a direct and/or straight connection between the two respective surfaces of the metal component and the plastic component connected to each other by means of the silicone seal. Accordingly, a spring element may be additional silicone material besides material needed to just fluid-tight fill a gap between the plastic component and the metal component. The silicone spring element can be configured to accommodate relative movement and/or expansion of the plastic component versus the metal component by a shape change. In particular, the silicone spring element can accommodate the relative movement and/or expansion not only by deformation of the silicone material itself, such as stretching or compression, but by changing and/or deforming its outer and/or cross-sectional shape. A silicone seal providing a spring effect is, for example, not a flat layer and/or has more flexibility than just a (massive) silicone due to its inherent flexibility. A labyrinth seal may provide improved fluid tightness between the metal component and the plastic component. In addition, a labyrinth seal may offer an especially robust connection between the metal component and the plastic component. For example, a labyrinth seal may comprise a channel wherein the plastic component or metal component is partially arranged. This may improve the connection between the components by providing an at least partially interlocking connection.

Another preferred embodiment of the tub, the silicone seal forms at least one channel with two opposing walls, in which at least a section of the plastic component is arranged/received. In this case, the silicone seal cannot only form a material bond between the two components but also an interlocking connection. The channel and the two opposing side walls can be a part of or constitute the previously described labyrinth seal.

In another preferred embodiment of the tub, the silicone seal forms at least one channel with two side walls, in which at least a section of the metal component and/or the metal component is arranged/received. This configuration may offer advantageous due to the usually higher thermal expansion coefficient of the metal component in comparison to the plastic component. Further, it may also provide an interlocking connection and/or can be part of or constitute a labyrinth seal.

In another preferred embodiment of the tub, the tub is configured to be associated with a lid, wherein the tub comprises a lid silicone seal arranged to provide a fluid seal between the lid and the tub when the lid is attached to the tub, in particular in a closed position. This may reduce or prevent any unintended leakages between the tub and a closed lid. For example, the lid can be removable attached and/or attached so that it can be moved between an open and a closed position. In particular, the tub can comprise a part of a pivot mount of the lid. The lid can be pivoted between an open and closed position. For example, the lid can be attached by means of a pivot connection or a snap-on connection to the tub. The lid silicone seal can be attached to the plastic component, in particular an upper side of the plastic component and/or an upper edge. In particular, the lid silicone seal can be arranged around an upper circumference of the tub. The lid silicone seal can be configured to seal a connection between the lid (in particular in a closed position) and the tub, in particular a tub body, in a substantially fluid tight manner.

Another preferred embodiment of the tub, the lid silicone seal and the silicone seal attaching the plastic component to the metal component are an integral one-piece component. Accordingly, the number of parts and/or manufacturing steps can be reduced. This can also be described as the silicone seal extending along the plastic component at least nearly up to the upper edge, exactly to the upper edge or slightly beyond the upper edge. The upper edge can be an end of the side walls, in particular an upper end. Again, the upper direction can be defined by the bottom wall and/or the reception space for the liquids. Preferably, the lid silicone seal is arranged on a inner side of the upper edge. The side walls can be partially or completely covered by the silicone seal on the side facing the reception space (e.g., the inside). Accordingly, the silicone seal can cover the complete inside of the plastic component (and optionally also the metal component) and end in an upper lid silicone seal for sealing a connection between the tub and an attached lid.

A second aspect of the invention relates to an apparatus for humidifying a flow of air for delivery to a patient. Said apparatus can comprise a tub according to the first aspect of the invention. Additionally, the apparatus can comprise a heating element to heat liquid received within this tub. This apparatus can also be called a humidifier. The humidifier can also comprise the tub. Preferably, the humidifier is part of a respiratory system, in particular a system for the treatment of a respiratory disorder in a patient. Usually, this system comprises a blower for delivering pressurized breathable gas to a patient, wherein the humidifier can increase the humidity and/or temperature of this gas. For this purpose, the humidifier comprises a liquid reservoir that is configured to heat the liquid contained in the reservoir. Since the apparatus according to the second aspect of the invention can comprise the tub according to the first aspect of the invention, improvements, features and embodiments of the first aspect can be considered as examples and embodiments of the second aspect of the invention, and vice versa.

For example, the heating element can be designed to heat the metal component of the tub. This allows the heat transfer to the liquid. In one embodiment, the heating element is an electrical heatable plate. Exemplary means to heat the metal component are electromagnetic induction, by directly applying an electrical current to the metal component and/or by heat transfer, in particular direct heat transfer, preferably from a hot plate of the heating element.

A third aspect of the invention relates to an apparatus for treating a respiratory disorder in a patient. This apparatus can comprise a patient interface, a controllable motor blower configured to generate a supply of air at positive pressure relative to ambient pressure and a tub according to the first aspect to the invention. Alternatively or additionally, the apparatus for treating a respiratory disorder in a patient can also comprise the apparatus according to the second aspect of the invention, which comprises a tub according to the first aspect of the invention. Therefore, improvements, features and embodiments of the first and second aspect can be considered as examples and embodiments of the third aspect of the invention and vice versa.

A fourth aspect of the invention relates to a method for manufacturing a humidifier tub configured to receive a volume of liquid. Preferably, the method is used to manufacture a tub according to the first aspect of the invention. Therefore, the method according to the fourth aspect of the invention is suitable to manufacture improvements, features and embodiments of the first aspect. Accordingly, any improvements, features and embodiments of the first aspect can be considered as examples and embodiments of the fourth aspect of the invention and vice versa. In particular, the tub according to the first aspect of the invention can comprise any feature manufactured when employing the method according to the fourth aspect of the invention.

Preferably, the method according to the fourth aspect of the invention comprises at least the step of providing at least one metal component; providing at least one plastic component; and attaching the at least one plastic component to the at least one metal component in a fluid tight manner by means of a silicone seal, such that the metal component and the plastic component together form a fluid tight space for receiving said volume of liquid. This method is cost effective and fast, since connection means and sealing means between the metal component and the plastic component do not have to be manufactured and/or mounted separately. In addition, a particular robust and light tub can be created.

For example, the two components can be attached to each other by applying the silicone to one or both components. The two components can be attached to each other by means of liquid silicone rubber introduced between the two components, which hardens to form the silicone seal. The silicone seal can also form the space for receiving said volume of liquid together with the metal component and the plastic component. For example, the silicone seal can be part of the side walls limiting the reception space for the liquid.

In a further preferred embodiment of the method according to the fourth aspect, the plastic component and the metal component are pre-manufactured and inserted into a tool, wherein the components are connected to each other by introducing silicone into a connection region between the metal component and the plastic component, in particular by introducing liquid silicone rubber into a region between the metal component and the plastic component or by introducing silicone to attach two respective regions of the metal component and the plastic component. The silicone can be injection molded for that purpose, especially as liquid silicone rubber. Between can relate to a connection space between both components at otherwise adjacent surfaces. Please also refer to the further aspects of the invention for possible arrangements of the silicone seal, which predetermines the arrangement and/or introduction of silicone between the components. A connection region can also be defined as a region where the metal component and the plastic component would and/or could at least partially touch each other without the silicone seal to form the reception space of the tub.

In a further preferred embodiment of the method according to the fourth aspect, the tub is manufactured in a multi-component injection molding process, in particular comprising injection molding a first component in a first injection molding step, injection molding a second component in a second injection molding step and introducing a third component, wherein the first component preferably is the plastic component, and wherein the second component preferably is the silicone seal, and wherein the third component preferably is the metal component or a metal blank that is formed into the metal component. Such a manufacturing method is fast. In particular it may not necessarily require different tools for the different components and/or for the silicone seal.

Preferably, the silicone is injection molded, in particular as liquid silicone rubber, between the metal component and the plastic component. Alternatively, the silicone seal can be formed after any injection molding process, for example by an applicator.

In a further preferred embodiment of the method according to the fourth aspect, first the plastic component is injection molded and then the metal component is introduced into an injection molding tool and then afterwards a silicone seal is injection molded so as to connect the plastic component and the metal component or first the metal component is introduced into an injection molding tool and then the plastic component is injected molded and then afterwards the silicone seal is injected molded so as to connect the plastic component and the metal component. In particular, the silicon seal is injection molded on the plastic component and the metal component/metal blank present in an injection molding tool. Preferably, the injected molding of the silicone seal is the last manufacturing step. For example, a multi-component tool can first be used to injection mold the plastic component. Afterwards, for example, a half of the multi-component injection tool is changed and/or movable parts are added or removed from the tool. In addition, either a metal blank designed to be formed into the metal component or the metal component itself—in its final shape—is inserted into the multi-component injection tool. Afterwards, liquid silicone is injected into the multi-component injection tool to form the silicone seal between the metal component and the plastic component. As is apparent, in this manufacturing process it is not necessary to extract any components from the multi-component injection tool before the tub is finished and/or to exchange the tool itself completely. Accordingly, the tub can be continuously formed/manufactured in one injection molding machine. Such a method can be especially cost effective.

In a further preferred embodiment of the method according to the fourth aspect, during the multi-component injection molding process, the first component is a plastic material injected in a two component injection tool and the second component is a silicone material, in particular silicone rubber, injected into the two component injection tool and the metal component or a metal blank is inserted as the third component into the two component injection tool. The metal component can be inserted as a rigid plate, in particular as a non-injection molded insert. For example, a pre-manufactured metal component or a metal blank can be used. The third component can be considered or designated as an insert and/or non-injection molded component.

Generally, in the method according to the fourth aspect a metal blank instead of a finished metal component can be used. In particular, the metal blank can be a flat metal sheet. If a metal blank is used, it can preferably be formed during the injection molding of the plastic component and/or the silicone seal to achieve its final shape; e.g., to be formed into the metal component. For example, the injection molding of the plastic and/or the silicone can deform a metal sheet into a dome-shaped metal component. Such a method can be especially cost effective. This process can require only one tool, in particular with a removable part, or the tool can be exchanged in between.

In a further preferred embodiment of the method according to the fourth aspect, the method involves using a molding tool comprising two or more parts and wherein, particularly if more than two mold parts are used, one or more of the mold parts are replaced and/or moved for molding the different parts/components of the tub. For example, this method and/or molded tool can comprise a sliding member, an exchange of the tool part by another tool part, particularly with a different geometry, and/or switching a half shell of the tool body by another half shell. During the process/method and/or exchange/replacement/movement of tool parts, any intermediate product can preferably remain in the tool, in particular in an unmoved part and/or a part remaining in the injection molding apparatus.

In a further preferred embodiment of the method according to the fourth aspect, the silicone is applied to the metal component and the plastic component by means of a silicone coating tool and the silicone coating tool is used to deform the metal into the desired final shape, in particular a shape with at least a dome-shape of the surface of the metal part facing away from the holding space. The metal can be a metal blank, such as a flat metal sheet. Preferably, the silicone coating tool can be an injection molding tool. Even more preferred, the silicone coating tool can be the same or the at least part of the tool used to injection mold the plastic component and/or silicone seal. Preferably, the silicone coating tool is the before described multi-component injection tool. The deformation of the metal component or metal blank into its desired final shape can be done before, after or during the application, in particular the injection of the silicone. Alternatively to forming the metal component or metal blank by means of the injection of the plastic into the tool, the metal component or metal blank can also be formed by the tool itself, for example in a separate step, in particular by closing the tool and/or moving a part of the tool. For example, two half of an injection molding tool can be closed with sufficient force to deform the metal component or metal blank in its desired final shape.

In a further preferred embodiment of the method according to the fourth aspect, an injection molding apparatus used for providing, in particular manufacturing the plastic component, is also used for applying the silicone. In particular, the injection molding apparatus can be used to apply the silicone to both the plastic component and the metal component. Preferably the same injection molding apparatus is used to manufacture the complete tub.

In a further preferred embodiment of the method according to the fourth aspect, before the attaching of the plastic component to the metal component by means of the silicone, an adhesion promoting agent is applied to at least a section of the plastic component and/or the metal component. In particular, the adhesion promoting agent can be applied to a section directly adjacent and/or facing a connection space between the two components. For further details of the arrangement of the silicone seal and therefore an appropriate arrangement of an adhesion promoting agent, please refer to the description of the other aspects of the invention, in particular the first aspect.

Preferably, the adhesion promoting agent is sprayed onto an appropriate surface of the plastic component and/or the metal components. In the context of the application of the adhesion promoting agent, the adhesion promoting agent can also be applied to a metal blank that is later formed into the metal component. Preferably, the plastic component, the metal component and/or the metal blank rest for a predetermined time for evaporation after production of the finished tub to avoid contact of the agent with a breathing gas. Alternatively or additionally, the reception space for the liquid can be cleaned after the application of the silicone seal. In other words: the reservoir can be washed after production, in particular after application of the silicone. As a further or alternative measure, the silicone can be coated to the complete surface that has been treated with an adhesion promoting agent.

Preferably, if the plastic component is formed in an injection molding step, the adhesion promoting agent is only applied to the metal blank or the metal component and the silicone, in particular liquid silicone rubber, is chosen to be able to attach to the plastic component without needing any further adhesion promoting agent.

In a further preferred embodiment of the method according to the fourth aspect, a mask is applied to at least a fraction of the metal component and/or plastic component, to seal portions that are intended to remain uncoated with a silicone, wherein preferably the mask is removed after the application of the silicone and/or of the adhesion promoting agent. This allows to reliably exclude certain sections of the surfaces from an attachment of the silicone. In particular, with a mask a non-area specific application method for the adhesion promoting agent, such as spraying it on in a chamber, can be used while still reliably defining which sections of the surfaces are actually treated. For example, the mask can be made from a masking tape. Alternatively or additionally, certain sections of the surfaces can be applied with an adhesion preventing agent. Some parts of the surfaces of the plastic component, the metal component and/or the metal blank can be non-adhesion treated in order to prevent attachment of the silicone.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.1 Humidifier Overview

Figure 5A:
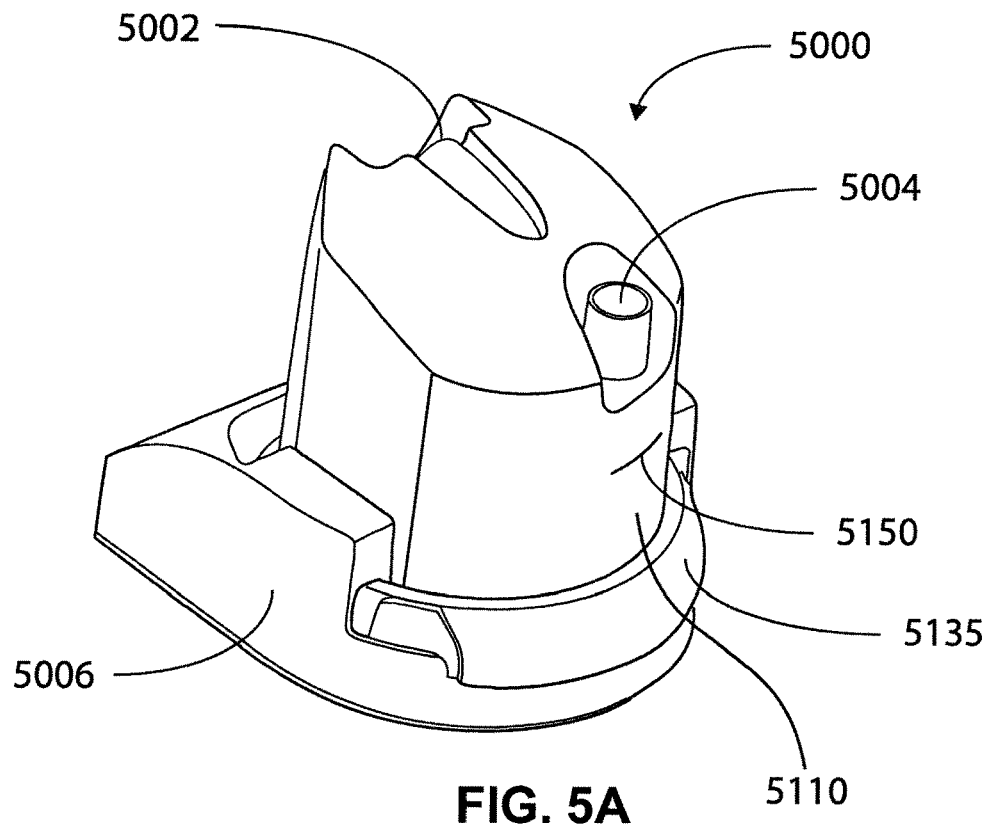
FIG. 5A shows an isometric view of a humidifier.

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

Figure 5B:
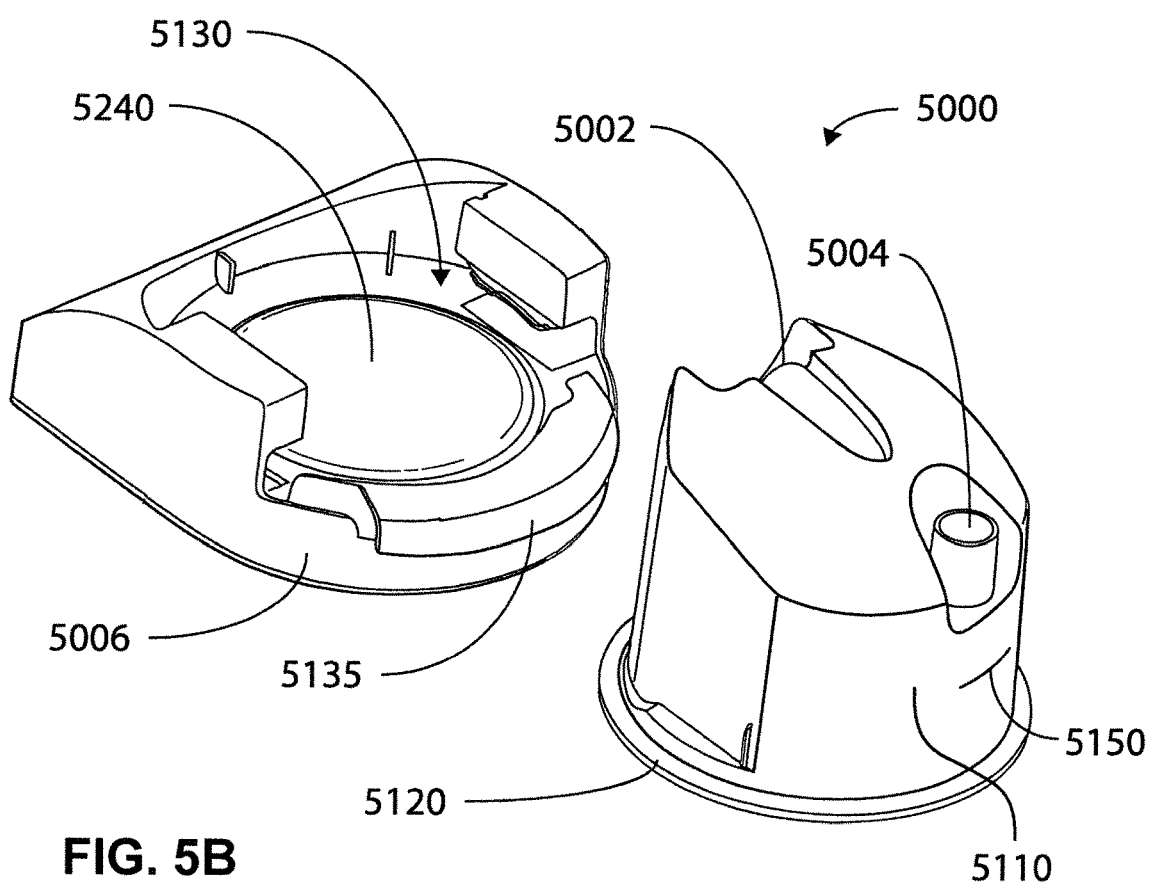
FIG. 5B shows an isometric view of a humidifier, showing a humidifier reservoir 5110 removed from the humidifier reservoir dock 5130.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

3.2 Humidifier Components

Figure 1A:
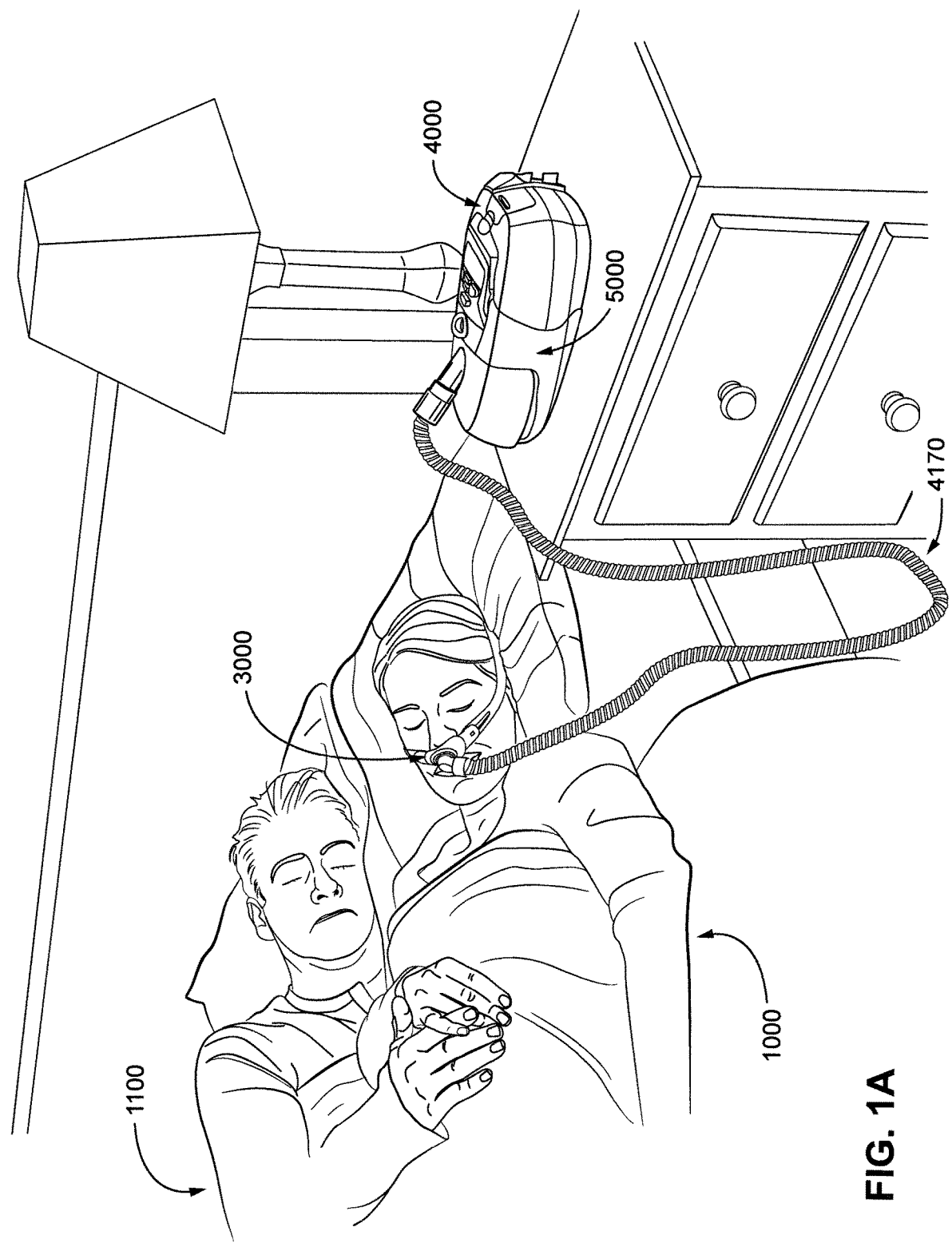
Figure 1B:
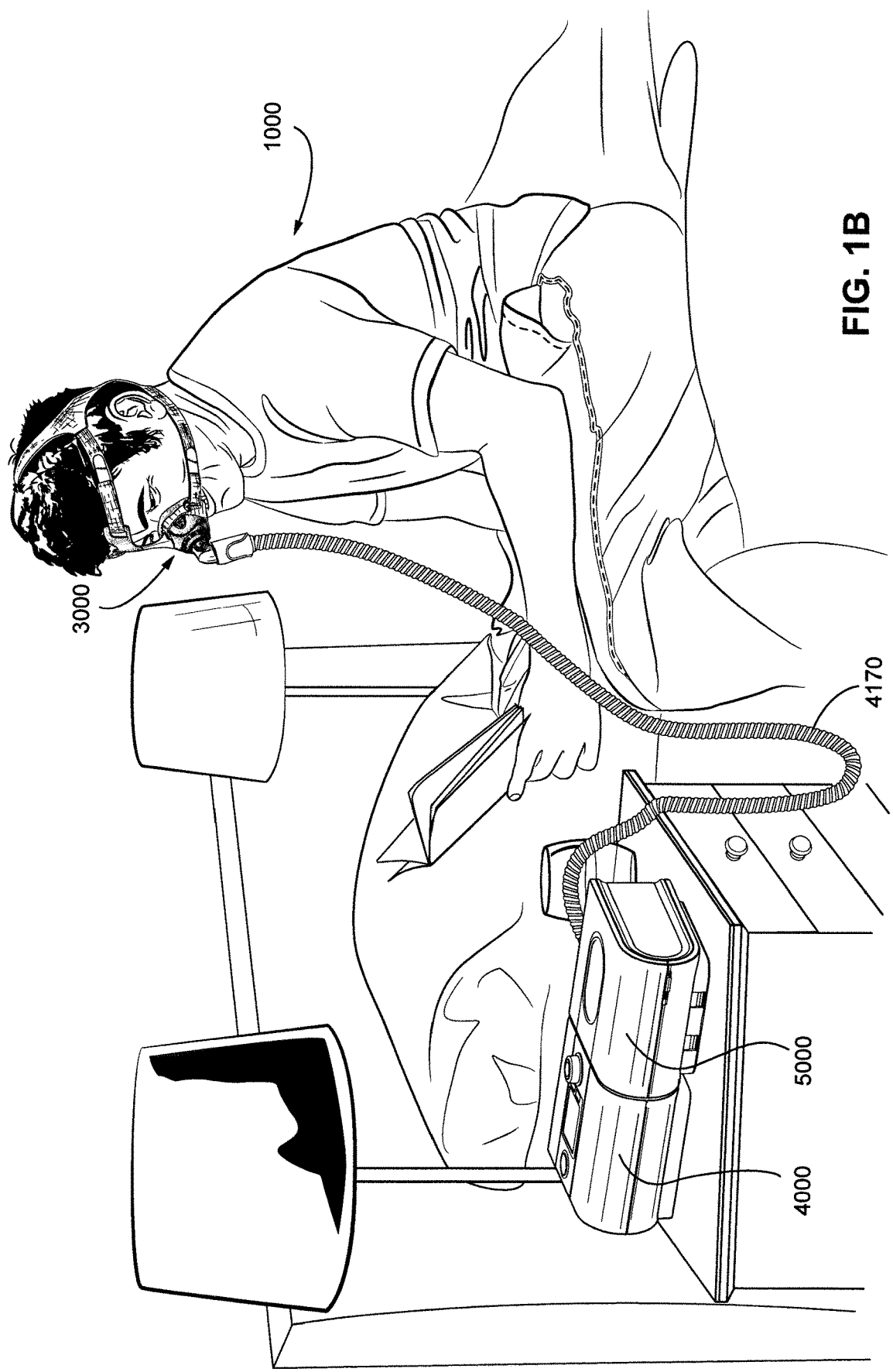
Figure 1C:

FIGS. 2, 3, 4 and 6 each show different embodiment of a tub configured to receive a volume of liquid for use in a humidifier. In particular, the shown embodiments of a tub 10 can be used or adapted to be used with a humidifier 5000 according to FIG. 1 and FIG. 5. The outer shape of tub 10 should be understood as mostly exemplary and can be adapted to conform to the shape of other components of the humidifier 5000.

As can be seen in FIGS. 2 to 4, and 6, tub 10 comprises at least one plastic component 12 and at least one metal component 14. The plastic component 12 and the metal component 14 together form a space 16 for receiving said volume of liquid. In the tub 10, the at least one metal component 14 and the at least one plastic component 12 are attached to each other by means of a silicone seal 18. In some embodiments, the silicone seal 18 is the only means of attachment between the plastic component 12 and the metal component 14.

As can also be seen in FIGS. 2-4,6, the tub 10 is generally trough shaped in order to receive a predetermined volume of liquid. Accordingly, in each embodiment, the metal component 14 forms at least a part of the bottom wall of the tub 10. Also accordingly, the plastic component 12 forms at least a part of one or more of the side walls of the tub 10. The remaining part of the one or more side walls of the tub 10 may be formed by the metal component 14 or other components of the tab 10. Generally, when the bottom wall is circular or oval-shaped, the tub 10 is considered to have one continuous side wall along the circumference of the bottom wall. The reference to more than one side walls is more applicable to the case of a square- or rectangular-shaped tub, where the side wall at each side of the rectangular may be considered as a separate side wall. The tubs illustrated in FIGS. 2-4 and 6 are represented in cross-sectional views only and can represent either case.

Usually, the tub 10 is placed with the metal component 14 directed downwards in order to be in a thermal contact with a heating plate. When the heating plate is activated, it heats the metal component 14 and thus the liquid contained in the space 16. The liquid can be inserted into the space 16 through the opening 20 at the top of the tub 10. The opening 20, the bottom wall and/or the reception space 16 can define respectively the upwards, downwards, inside and/or outside direction of the tub 10.

The silicone seal 18 attaches the plastic component 12 to the metal component 14 in a fluid tight manner. This is the reason why it is referred to as a "seal". However, sealing is not the only function that the component 18 fulfils. As mentioned, it also serves as attachment means between the plastic component 12 and the metal component 14. The silicone seal 18 also serves to at least partially compensate the different extent of thermal extensions and contractions of the metal component 14 and the plastic component 12 during a heating cycle of a humidifier. For example, the silicone seal 18 can be flexible and compensate by being stretched and/or contracted without breaking contact with the plastic component 12 and the metal component 14. In particular, the silicone seal 18 can maintain the seal between the plastic component 12 and the metal component 14 by accommodating such different thermal expansions and contractions of the plastic component 12 and the metal component 14, without allowing any fluid to leak outside of the space 16 trough a connection between those components.

As can also be seen in FIGS. 2-4 and 6, the plastic component 12 and the metal component 14 are only attached to each other by means of the silicone seal 18. Therefore, no additional attachment means are required. Even further, the plastic component 12 and the silicone seal 18 can be manufactured together in one injection molding tool, in particular in a common injection molding process. In that case, the metal component 14 can be provided into the injection molding tool as an insert. Accordingly, both the plastic component 12 and the silicone seal 18 are directly injection molded onto the metal component 14. For example, the plastic component 12 and the silicone seal 18 can be injection molded onto the metal component 14 in two successive molding steps. For example, first the silicone seal 18 can be injection molded onto the metal component 14 and afterwards the plastic component 12 is injection molded, in particular onto the silicone seal 18. As an alternative, first the plastic component 12 is injection molded and then the silicone seal 18 is injection molded between the two components 12 and 14. These examples also allow to manufacture the plastic component 12 independent of the other components. Another sequence is also possible. For example, the plastic component 12 can be injection molded first, then the metal component 14 is introduced into the tool and afterwards the silicone seal 18 is injection molded inbetween the two components 12, 14. The silicone seal 18 can in each instance serve to connect the two components 12, 14 to each other, in particular in a fluid tight manner. For this purpose, the silicone can be configured to attach itself to the plastic of the plastic component 12 while the metal component 14 can be treated with an adhesion promoting agent to allow for the attachment of the silicone. Preferably, the silicone seal 18 is manufactured from liquid silicone rubber.

Figure 2:
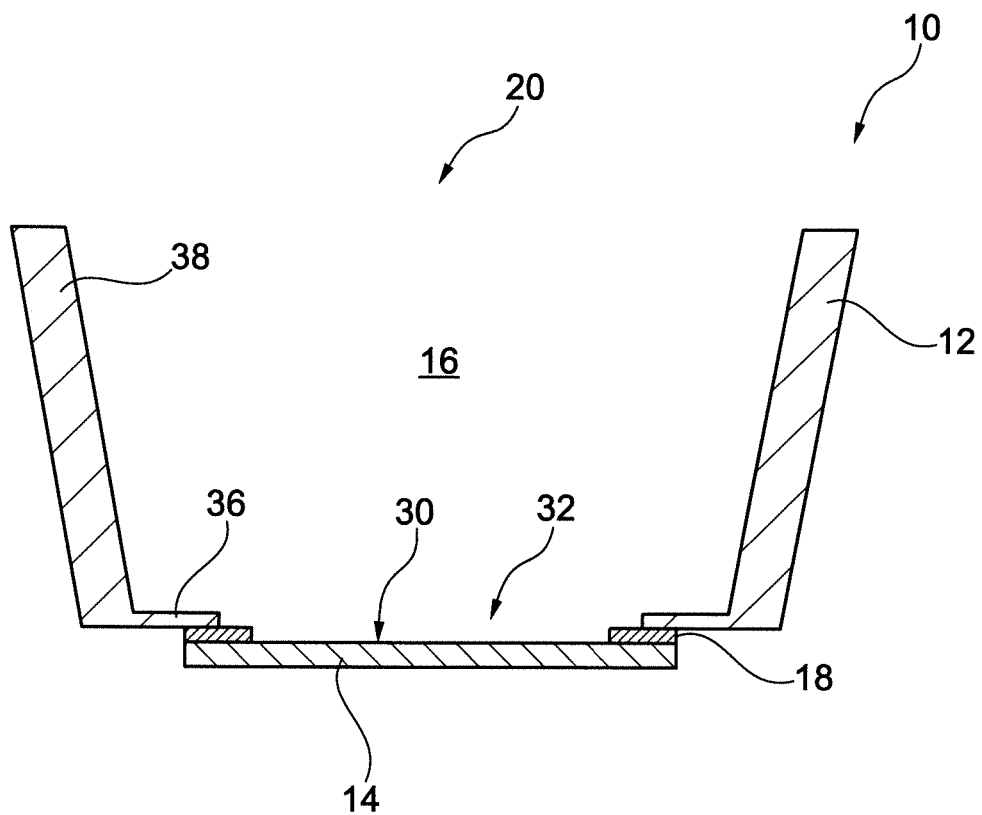
FIG. 2 shows in a cross-sectional schematic view a tub configured to receive a volume of liquid for use in a humidifier.

As can be seen in FIG. 2, the silicone seal 18 substantially closes a gap between the metal component 14 and the plastic component 12. In particular, the silicone seal 18 is at least arranged at an overlap region of the plastic component 12 and the metal component 14 when seen from a bottom or top view. Since the tub 10 usually rests on the metal component 14 during use, such a construction is especially robust because the weight of the tab strengthens the connection between the two components during use.

In the embodiment according to FIG. 2, the silicone seal 18 is formed as an annular member that covers the outer periphery of the inner side of the metal component 14. Accordingly, a middle region of the metal component 14 is not covered with the silicone, thus not inhibiting heat transfer to a liquid in the space 16. In the present embodiment, the bottom of tub 10 is of a generally round shape. However, as mentioned above, the tub 10 may also have any other shapes, such as a basic rectangular or square shape, particularly when seen in a bottom view.

Figure 3:
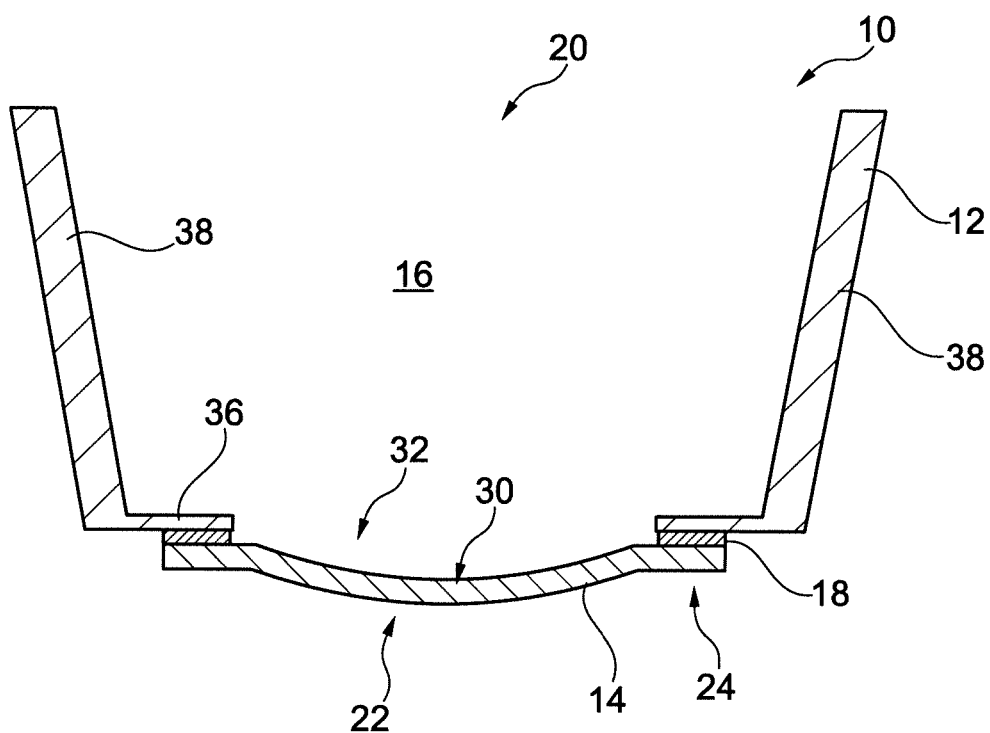
FIG. 3 shows in a cross-sectional schematic view another embodiment of a tub for use in a humidifier.

FIG. 3 shows another embodiment of the tub 10 in a schematic cross-sectional view. As can be seen in FIG. 3, in this embodiment the metal component 14 is not flat (as is the case in FIG. 2), but has a dome-shaped region 22. This dome-shaped region 22 may provide improved contact to a heating plate located below the tub 10. Accordingly, the heat efficiency of a humidifier with such a tub 10 can be improved.

In FIG. 3, the metal component 14 is only dome-shaped outwardly from the space 16 in a region not overlapping with the plastic component 12 in a bottom view. An outer annular section 24 of the metal component 14 has a similar planar shape to the metal component according to the embodiment of FIG. 2. This allows for an easier and reliable connection between the metal component 14 and the plastic component 12 with the silicone seal 18. In alternative embodiments, the entire metal component 14 may be dome-shaped. Such a dome-shaped metal component may be easy to manufacture.

The dome-shape of the metal component 14 according to the embodiment of FIG. 3 can be formed directly in the injection molding process of the silicone seal 18 and/or the plastic component 12. For example, a flat metal sheet blank can be formed, by the pressure of the injection molding and/or the closing of an injection molding tool, into the dome-shape.

Figure 4:
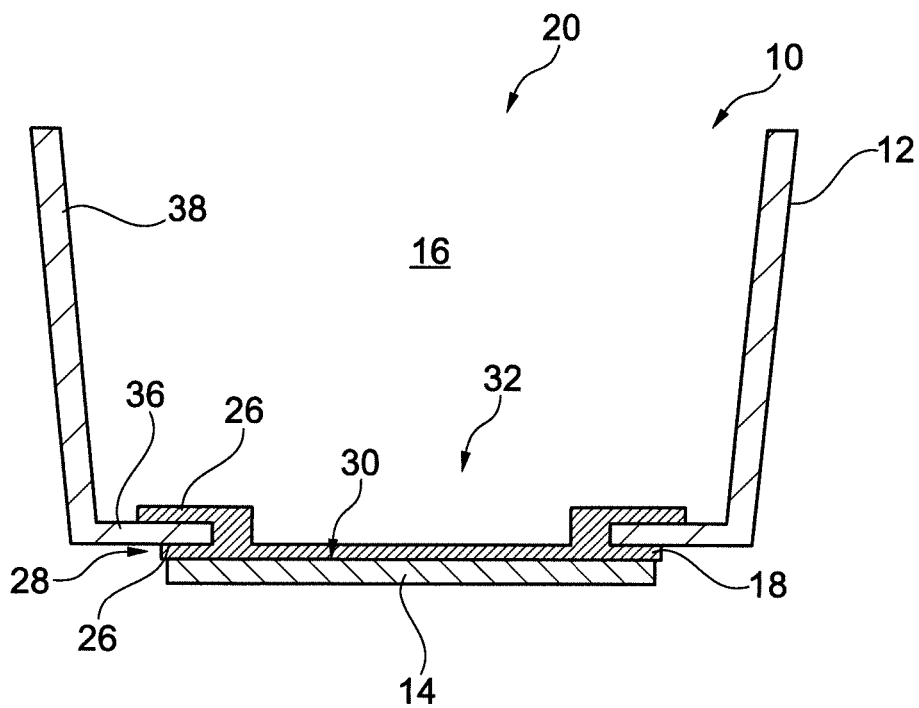
FIG. 4 shows in a cross-sectional schematic view another embodiment of a tub for use in a humidifier.

FIG. 4 shows another embodiment of the tub 10. In the case of FIG. 4, the silicone seal 18 provides a type of labyrinth seal whose sealing between the plastic component 12 and the metal component 14 can be especially reliable. Even if parts of the area of the silicone seal 18 according to this embodiment are damaged in the overlap region of the plastic component 12 and the metal component 14, there is still some form of redundancy to prevent unintended leakages of fluid from the space 16. For that purpose, the silicone seal 18 has two opposite walls 26 that form a channel 28. In that channel 28, a part of the plastic component 12 is received. This provides an interlocking connection of the components by means of the silicone seal 18. Alternatively or additionally, the metal component 14 could also be received in such a channel formed by two side walls of the silicone seal 18 (not shown in FIG. 4).

As can also be seen in FIG. 4, the therein shown embodiment of tub 10 comprises a silicone seal 18 that covers the whole surface 30 of the metal component 14 facing the space 16. Whilst not strictly necessary, the silicone seal 18 in such a configuration can prevent direct contact of the liquid contained in space 16 with the metal component 14. Accordingly, it is possible to use a metal for the metal component 14 that is less corrosive resistant than the metal used in the other embodiments where the metal component 14 can have direct contact and is exposed to the liquid in the space 16.

While the lower side wall 26 of the silicone seal 18 according to FIG. 4 also covers the surface 30 of the metal component 14 facing the space 16, such a covering is not necessary to achieve the corrosion protection of the metal component 14 in said embodiment, as the covered portion of the component 14 is not directly exposed to the heated liquid. However, in the present case this lower of the opposite walls 26 also constitutes part of the labyrinth seal and improves the connection between the metal component 14 and the plastic component 12.

Figure 6:
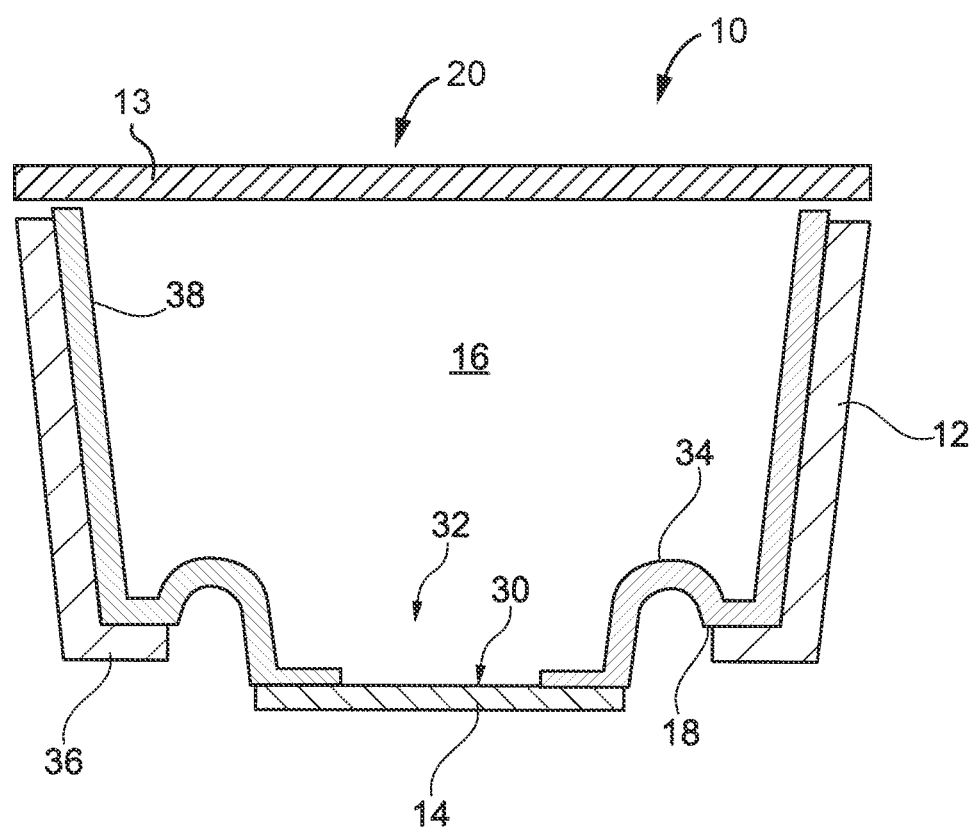
FIG. 6 shows in a cross-sectional schematic view of an alternative embodiment of a tub to that in FIGS. 2-4, for use in a humidifier.

Alternatively to the embodiments of FIGS. 2, 3 and 4, there may not be an overlapping between the metal component 14 and the plastic component 12, and the metal component 14 can be limited so as to not extend radially beyond an inner edge of the plastic component 12. In this case (shown in FIG. 6) there may be a gap between the outer peripheral edge of the metal component 14 and the inner peripheral edge of plastic component 12, which can be bridged by the silicone seal 18. Because of the flexibility of the silicone seal 18, in that case the metal component 14 can flex in space, including moving towards, and away from the space 16, through a bottom hole of the plastic component 12. This can provide a form of spring effect that may improve the connection between the metal component 14 and a hot plate on which the tub 10 is placed. This may allow to use tubs manufactured with higher manufacturing tolerances. The gap can be substantial, as shown in FIG. 6, or can be minimised to a point where the peripheral edges of the metal component 14 and the plastic component 12 substantially touch each other. (not shown in FIG. 6)

In the case of the embodiment of FIG. 6, element 34 provides the discussed spring function of the silicone seal 18. In the shown embodiment, the length of the spring element 34 exceeds the gap between the metal component 14 and the plastic component 12, which needs to be breached. This excess length, together with the flexibility of the silicone seal, can cause at least partially the spring effect. The spring element 34 can include a curved, or otherwise bent, section of the silicone seal 18. The curved section 34 can deform, in particular by changing its radii. Therefore, the embodiment of the silicone seal 18 according to FIG. 6 not only allows an upward movement of the metal component 14 due to a possible compression and/or stretching of the silicone seal 18 but also due to an excess length and a deformation of its cross-sectional shape. Therefore, the metal component 14 can move relatively freely with respect to the plastic component 12 within the hole 32 in order to shift its position for a particularly good contact to a hot plate positioned below the tub 10. Therefore, the heating efficiency of such a tub 10 may be increased. In addition, such a tub 10 may be easier to insert in and extract from a humidifier with less force and/or with a lower risk of damaging it.

Preferably, the silicone seal 18 is made from a medical grade silicone. The thickness of the silicone seal is preferably between 0.01 and 0.2 mm, preferably less than 0.05 mm. With such a thickness, the silicone seal 18 does not unnecessarily inhibit heat transfer from the metal component 14 to the liquid in the space 16, even if it covers any section of the surface of the metal component 14, which otherwise would be in contact with the liquid. Even with such a thin thickness, the silicone seal 18 is sufficiently strong to attach the plastic component 12 and the metal component 14 while forming a reliable seal.

As can be seen in the figures showing the embodiments of tub 10, the plastic component 12 can be essentially through-shaped, having a bottom wall 36 and surrounding side wall 38 extending from said bottom wall 36. The bottom wall 36 has the already described through-hole 32, which is closed by the metal component 14 and/or the silicon seal 18. In FIGS. 2-4, the dimension of the metal plate 14 is larger than the through-hole 32. Such a configuration may offer benefits since it can limit the maximum movement rage of the metal component 14 in an upward direction. The bottom wall 36 of the plastic component can act as an end stop for the metal component 14. In addition, the bottom wall 36 offers a surface that can easily be used for reliable attachments of the metal component 14 by means of the silicone seal 18. However, in an alternative embodiment, the plastic component 12 may only comprise the side walls 38 and not the bottom wall 36. Such a plastic component 12 may be cheaper and faster to manufacture. In that case, the metal component 14 can also be located essentially in the through-hole 32 of the plastic component 12. In this case a portion of the silicone seal 18 may need to be laid over a portion of the side wall 38. This could be done by attaching the silicone seal 18 to a portion of at least one of the inner or the outer side of the side wall 38.

In the shown embodiments, the metal component 14 is arranged on the outside of the plastic component 12 with respect to the space 16. However, the metal component 14 can also be arranged on the inside.

In other embodiments, the silicone seal 18 can cover further surfaces of the plastic component 12 and/or the metal component 14. For example, the silicone seal 18 could cover essentially the complete inner surface of the side walls 38 and the bottom wall 36 of the plastic component 12. Again, the inner surface in this case is the surface facing the space 16. In that case, the silicone seal 18 could additionally also protect the plastic component 12 from exposure to the heated liquid. Such a protective cover may offer an increased scratch resistance and may also facilitate a cleaning of the space 16. Furthermore, the silicone seal 18 could also extend nearly up to the upper edge of the side walls 38 or even slightly beyond this edge. In that case, the silicone seal 18 can also form a lid silicone seal for a lid 13 attached to the plastic component 12 at its upper side. Such a lid can be used to close the opening 20. The lid silicone seal is preferably part of the silicone seal 18 and can then prevent unintended leakage between the lid and the plastic component 12. This possibly allows the change of an orientation of the tub 10 without any loss of liquid. This may facilitate more comfortable handling of the tub 10 when there is liquid contained within the space 16.

If the liquid silicone seal 18 also comprises the lid silicone seal in a one-piece construction, they can be manufactured together in one step. For example, the silicone seal 18 can be formed together with its lid silicone seal in one injection molding step.

3.2.1.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may at least partially be formed by tub 10. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred milli-litres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

3.2.1.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, such as plate 14, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

3.2.1.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

3.2.1.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

3.2.1.5 Humidifier Transducer(s)

Figure 5C:
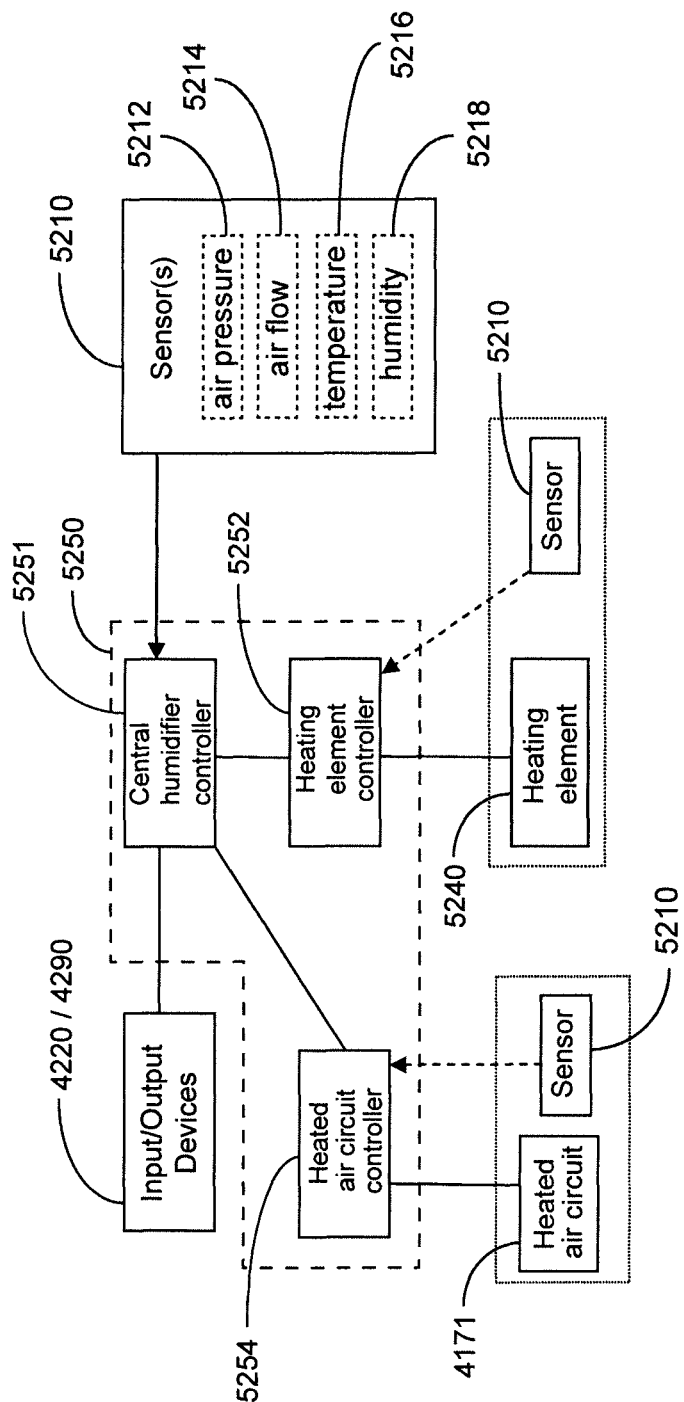
FIG. 5C shows a schematic of a humidifier.

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

3.2.1.5.1 Pressure Transducer

One or more pressure transducers 5212 may be provided to the humidifier 5000 in addition to, or instead of, a pressure sensor 4272 provided in the RPT device 4000.

3.2.1.5.2 Flow Rate Transducer

One or more flow rate transducers 5214 may be provided to the humidifier 5000 in addition to, or instead of, a flow rate sensor 4274 provided in the RPT device 4000.

3.2.1.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

3.2.1.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

3.2.1.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

3.2.1.7 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

3.3 Glossary

For the purposes of the present technology disclosure, in certain forms of the present technology, one or more of the following definitions may apply. In other forms of the present technology, alternative definitions may apply.

3.3.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient. Leak can also relate to the unintended flow of liquid from a humidifier, especially a tub for receiving a volume of liquid of the humidifier.

Patient: A person, whether or not they are suffering from a respiratory condition.

Ventilator: A mechanical device that provides pressure support to a patient to perform some or all of the work of breathing.

3.3.1.1 Materials

Siliconee or Siliconee Elastomer: A synthetic rubber. In this specification, a reference to siliconee is a reference to liquid siliconee rubber (LSR) or a compression moulded siliconee rubber (CMSR). One form of commercially available LSR is SILASTIC (included in the range of products sold under this trademark), manufactured by Dow Corning. Another manufacturer of LSR is Wacker.

Polycarbonate: a thermoplastic polymer of Bisphenol-A Carbonate.

3.3.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include siliconee or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

3.4 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

3.5 Reference Signs List 10 tub
12 plastic component
14 metal component
16 space
18 silicone seal
20 opening
22 dome-shaped area
24 outer annular section
26 opposite side walls
28 channel
30 surface
32 through-hole
34 spring element
36 bottom wall
38 side wall

The invention claimed is:

1. A tub configured to receive a volume of liquid for a humidifier, comprising
   at least one plastic component having a bottom wall with a through hole; and
   at least one metal component,
   wherein the at least one metal component and the at least one plastic component are attached to each other in a fluid tight manner by means of a silicone seal, such that the at least one metal component and the at least one plastic component together form a space for receiving said volume of liquid; and
   wherein at least a majority of an inner surface of the at least one metal component facing the space for receiving said volume of liquid is coated with the silicone seal, and
   wherein the through hole is closed by said at least one metal component and said silicone seal.

2. The tub according to claim 1, wherein
   the silicone seal provides a fluid tight connection between the at least one plastic component and the at least one metal component.

3. The tub according to claim 1, wherein
   the silicone seal has a thickness between 0.01 mm and 0.2 mm.

4. The tub according to claim 1, wherein
   at least a section of the at least one metal component and/or a section of the at least one plastic component is treated with a silicone adhesion promoting agent.

5. The tub according to claim 1, wherein
   the silicone seal is formed from liquid silicone rubber.

6. The tub according to claim 1, wherein
   the at least one plastic component and/or the at least one metal component are rigid.

7. The tub according to claim 1, wherein
   the at least one plastic component is trough shaped, and includes one or more side walls, extending from said bottom wall.

8. The tub according to claim 1, wherein
   the tub is trough shaped, having the bottom wall and one or more side walls, wherein the at least one plastic component is sleeve shaped and forms the one or more side walls.

9. The tub according to claim 7, wherein
   the at least one metal component is attached to an inner side or an outer side of said one or more side walls and/or to an inner side or an outer side of said bottom wall.

10. The tub according to claim 1, wherein
    the at least one metal component is shaped as a metal plate.

11. The tub according to claim 1, wherein
    at least a portion of the at least one metal component is dome shaped in an outward direction.

12. The tub according to claim 1, wherein
    the at least one metal component and the at least one plastic component are only attached to each other by means of the silicone seal.

13. The tub according to claim 1, wherein
    at least a portion of the at least one metal component and at least a portion of the at least one plastic component overlap each other, and wherein the silicone seal is arranged to extend at least between the overlapping portions of the at least one metal component and the at least one plastic component.

14. The tub according to claim 1, wherein the silicone seal covers at least a portion of the at least one metal component, wherein the portion of the at least one metal component is not overlapping with the plastic component; and/or the silicone seal covers at least a portion of the at least one plastic component, wherein the portion of the plastic component is not overlapping with the at least one metal component.

15. The tub according to claim 1,
wherein the silicone seal further covers at least a further portion of the at least one metal component and/or the at least one plastic component for surface protection, including any surface forming the space of the tub.

16. The tub according to claim 1, wherein
an entirety of the inner surface of the at least one metal component facing the space for receiving said volume of liquid is coated with the silicone seal, in the form of a silicone layer on the surface of the at least one metal component.

17. The tub according to claim 1, wherein
the silicone seal is formed as a labyrinth seal.

18. The tub according to claim 1, wherein
the silicone seal forms at least one channel with two side walls, in which at least a section of the at least one plastic component and/or the metal component is arranged/received.

19. The tub according to claim 1, wherein
the silicone seal is formed as a seal providing a spring effect, by comprising a silicone spring element.

20. The tub according to claim 1, wherein
the tub is configured to be associated with a lid, wherein the tub comprises a lid silicone seal arranged to provide a fluid seal between the lid and the tub, when the lid is attached to the tub in a closed position.

21. The tub according to claim 20, wherein
the lid silicone seal and the silicone seal attaching the plastic component to the metal component comprise a one-piece component.

22. An apparatus for humidifying a flow of air for delivery to a patient, said apparatus comprising:
the tub according to claim 1;
a heating element to heat liquid received within said tub.

23. An apparatus for treating a respiratory disorder in a patient comprising:
a patient interface;
a controllable motor-blower configured to generate a supply of air at a positive pressure relative to ambient pressure; and
the tub according to claim 1.

24. The tub according to claim 1, wherein a portion of the inner surface is not covered by the silicone seal.

25. A method for manufacturing a humidifier tub configured to receive a volume of liquid, the method comprising:
providing at least one metal component;
providing at least one plastic component with a bottom wall and a through hole; and
attaching the at least one plastic component to the at least one metal component in a fluid tight manner by means of a silicone seal, such that the at least one metal component and the at least one plastic component together form a fluid tight space for receiving said volume of liquid,
wherein at least 70% of an inner surface of the at least one metal component facing the space for receiving said volume of liquid is coated with the silicone seal and wherein the through hole is closed by said at least one metal component and said silicone seal.

26. The method according to claim 25,
wherein the at least one plastic component and the at least one metal component are premanufactured and inserted into a tool, wherein the at least one plastic component and the least one metal component are connected to each other introducing silicone into a connection region between the at least one metal component and the at least one plastic component, by introducing liquid silicone into a connection region between the at least one metal component and the at least one plastic component.

27. The method according to claim 25,
wherein the tub is manufactured in a multi-component injection molding process, comprising injection molding a first component in a first injection molding step, injection molding a second component in a second injection molding step, and introducing a third component.

28. The method according to claim 27, wherein first the at least one plastic component being the first component is injection molded and then the at least one metal component being the third component is introduced and afterwards the silicone seal being the second component is injection molded so as to connect the at least one plastic component and the at least one metal component, or first the at least one metal component being the third component is introduced into an injection molding tool and then the at least one plastic component being the first component is injection molded and afterwards the silicone seal being the second component is injection molded so as to connect the at least one plastic component and the at least one metal component.

29. The method according to claim 27, wherein, during the multi-component injection molding process, the first component is a plastic material injected in a two-component injection tool and the second component is a silicone material, injected into the two-component injection tool and the third component is the at least one metal component or a metal blank is inserted as a further component into the two-component injection tool.

30. The method according to claim 27,
wherein the method involves using a molding tool comprising two or more mold parts, and wherein, where more than two mold parts are used, one or more of the mold parts is replaced and/or moved for molding the different components.

31. The method according to claim 25,
wherein the silicone is applied to the at least one metal component and the at least one plastic component by means of a silicone coating tool and wherein the silicone coating tool is used to deform the metal component or metal blank into a desired final shape with at least a convex shape of the surface of the metal component facing away from the holding space.

32. The method according to claim 25,
wherein an injection molding apparatus used for manufacturing the at least one plastic component is also used for applying the silicone.

33. The method according to claim 25,
wherein before the attaching of the at least one plastic component to the at least one metal component by means of the silicone seal, an adhesion promoting agent is applied to at least a section of the at least one plastic component and/or the at least one metal component.

34. The method according to claim 25,
a mask is applied to at least a fraction of the at least one metal component and/or at least one plastic component to shield portions that are intended to remain uncoated with silicone, wherein the mask is removed after the application of the silicone seal or after application of the adhesion promoting agent.

\* \* \* \* \*

UNITED STATES PATENT AND TRADEMARK OFFICE
CERTIFICATE OF CORRECTION

PATENT NO.        : 11,376,392 B2
APPLICATION NO.   : 15/961017
DATED             : July 5, 2022
INVENTOR(S)       : Andreas Kirchberger Page 1 of 1

It is certified that error appears in the above-identified patent and that said Letters Patent is hereby corrected as shown below:

In the Claims

Claim 1, Column 26, Line 16, "wherein at least a majority of an inner surface of the..." should read -- wherein at least 70% of an inner surface of the --

Signed and Sealed this
Sixteenth Day of August, 2022

Katherine Kelly Vidal
*Director of the United States Patent and Trademark Office*